United States Patent [19]
Schmidt et al.

[11] Patent Number: 4,536,090
[45] Date of Patent: Aug. 20, 1985

[54] OPTICAL MULTI-BEAM GAS MEASURING APPARATUS

[75] Inventors: Martin Schmidt, Bad Schwartau; Horst D. Hattendorff, Lubeck, both of Fed. Rep. of Germany

[73] Assignee: Drägerwerk Aktiengesellschaft, Fed. Rep. of Germany

[21] Appl. No.: 462,994

[22] Filed: Feb. 1, 1983

[30] Foreign Application Priority Data

Mar. 11, 1982 [DE] Fed. Rep. of Germany ....... 3208737

[51] Int. Cl.³ ............................................. G01N 21/61
[52] U.S. Cl. ..................................... 356/414; 250/339; 250/345; 250/373
[58] Field of Search .......................... 356/51, 409–411, 356/414, 416, 419, 432–437; 250/339, 343, 345, 373

[56] References Cited

U.S. PATENT DOCUMENTS

| | | | |
|---|---|---|---|
| 1,371,969 | 3/1921 | Furman | 350/170 |
| 2,974,227 | 3/1961 | Fisher et al. | 356/411 |
| 3,306,156 | 2/1967 | Glasser et al. | 250/373 X |
| 4,081,215 | 3/1978 | Penney et al. | 356/45 |

FOREIGN PATENT DOCUMENTS 13409  1/1982  Japan ................................. 350/170

OTHER PUBLICATIONS

*Measurement and Control,* vol. 2, No. 3, Mar. 1963, pp. 90–93.

*Primary Examiner*—F. L. Evans
*Attorney, Agent, or Firm*—McGlew and Tuttle

[57] ABSTRACT

An optical multi-beam gas measuring apparatus is intended for detecting specific content in a gas of extraneous gases which absorb the same wavelength of the measuring radiation. The apparatus comprises a source of radiation and a gas vessel through which the gas mixture to be measured is conducted and the radiation is detected. The radiation directed through the vessel is picked up by an exchangeable detecting unit which contains a prism for splitting radiation which has passed through the gas mixture into several partial beams corresponding to the number of gas components to be measured. A prism is selected for this purpose and it is used in association with optical filters arranged in the path of the beams in conjunction with detectors which are electronically arranged for detecting the selected gases and measuring the value thereof.

6 Claims, 5 Drawing Figures

OPTICAL MULTI-BEAM GAS MEASURING APPARATUS

FIELD AND BACKGROUND OF THE INVENTION

This invention relates in general to gas detectors and in particular to a new and useful optical multi-beam gas measuring device.

The specific purpose of a measuring apparatus in accordance with the present invention is to measure gases in which extraneous gases absorbing in the same wavelength region are admixed. For example, the alcohol content in exhaled air can very accurately be measured through infrared absorption of a wavelength of 3.4 microns. However, acetone traces, which may be present in the exhaled air due to sickness or excessive fasting, for example, may be mistaken at this wavelength for alcohol which is not present. Acetone may be detected by measuring the optical transmission at 3.25 microns, which wavelength is virtually no longer absorbed by alcohol.

In a prior art apparatus for measuring the proportion of a component of a mixture transmitting radiation, the beam is directed by optical means from a source of optical radiation through a gas vessel containing the mixture to be checked, to a following beam splitter by which the beam is split into two separate, parallel partial beams. Further, filters for selecting various wavelengths are provided in the paths of each partial beam, aside from other auxiliary means. Behind the filters, a collective lens for concentrating the partial beams is followed by a detector and a device for processing and evaluating the signal. A chopper is provided for alternately directing the signals of the partial beams to the processing device.

The beam splitter is embodied by a prism system comprising a rectangular central prism whose right-angle edge pointing against the radiation is positioned symmetrically in the radiation axis. The prism splits the beam by reflection at its surfaces into two partial beams which are at right angles to the axis of the original beam. Aside from the central prism, two equalsided right-angle lateral prisms are so positioned that upon entering a lateral prism, each partial beam is reflected from the hypotenuse face thereof at 90° to emerge parallel to the axis of the original beam. The manufacture of the central and lateral prisms as single-piece bodies as well as their mounting and adjustment are very expensive. Further, the prisms are highly sensitive to stresses. A re-equipment of the apparatus with partial beam filters suitable for other gases is also very expensive. (German AS No. 23 50 004).

SUMMARY OF THE INVENTION

The present invention is directed to a gas measuring apparatus intended for a variety of users and permitting a simultaneous measuring of various gases upon a simple re-equipment.

In accordance with the invention, there is provided an optical multi-beam gas measuring apparatus for measuring proportions of a gas mixture. The apparatus comprises an optical radiation source for directing the radiation through a vessel through which the gas mixture is directed. Radiation passes through the gases to a beam splitter or prism which splits the radiation into a plurality of partial beams which are guided by a collectable lens through optical filters and detectors of an electronic unit which indicates the characteristics and nature of the gases which are detected.

The inventive detecting apparatus includes component parts which are needed for adapting the apparatus to the varying number of gases to be measured, and to the specific measuring problem.

Since a prism is used as the beam splitter and optical filters are provided in the partial beam paths, a constructional unit is obtained which does not contain movable parts and can be made rugged and fixed in position. Through the prism, the measuring beam can be split into any number of partial beams, without the necessity of changing the dimensions of the prism.

Accordingly, it is an object of the invention to provide an improved optical multi-beam gas measuring apparatus for detecting various components of a gas mixture. In accordance with a method of the invention, the gas mixture is passed through a vessel and a radiation is passed through the gas which is split up by a prism into discreet partial beams which are passed through light filters and detectors which are effective to determine the characteristic of the gases of each of the split beams.

A further object of the invention is to provide a device for detecting gases of a gas mixture which comprises directing the gas mixture through a gas vessel and directing a radiation through the gases and through a beam splitter in the form of a prism which directs the gases through a discreet path and through optical filters and detectors for analyzing the characteristics of each path.

A further object of the invention is to provide a device for obtaining the characteristics of gases of a mixture which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
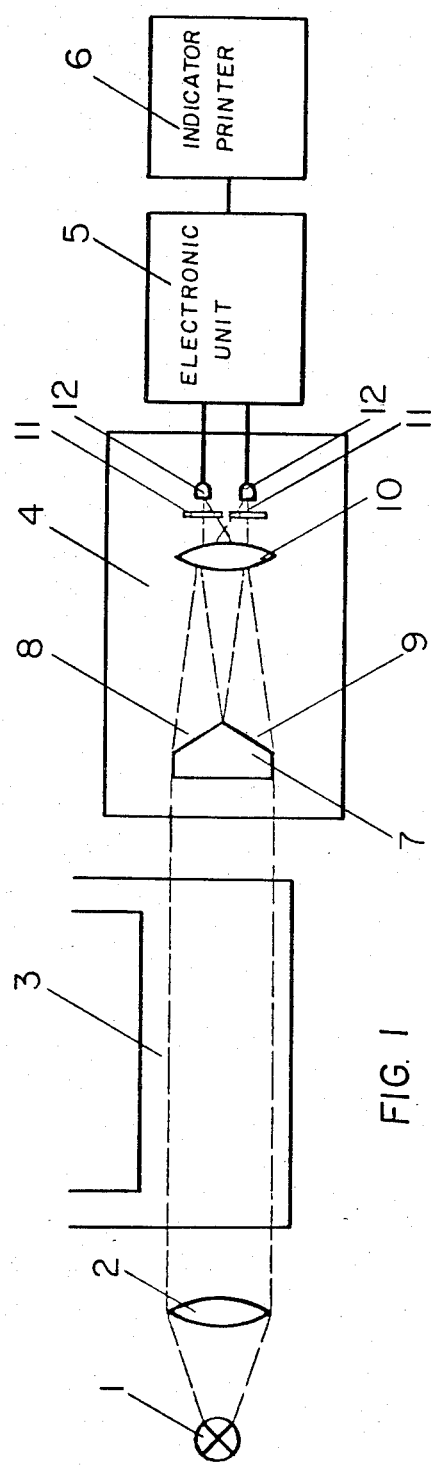
FIG. 1 is a diagrammatical indication of a multi-beam gas measuring apparatus for two wavelengths constructed in accordance with the invention.

Referring to the drawings in particular the invention embodied therein, in FIG. 1 comprises an optical multi-beam gas measuring apparatus for measuring proportions of a gas mixture which comprises an optical radiation source 1 disposed to direct radiation through a focusing lens 2 and a gas mixture which is directed through a gas vessel 3. Radiation is directed through a detecting device 4 which includes a beam splitter embodied by a prism 7 as well as a collective lens 10 which guides the beams which are split into partial beams which are directed through an optical filter 11, 11 and corresponding detectors 12, 12 from an electronic unit 5 which precedes an indicating unit 6 which together form a common exchangeable detecting device 4.

The function of an optical multi-beam gas measuring apparatus for two wavelengths will become evident from the construction thereof. The radiation source 1 emits light in the visible, ultraviolet, or infrared spectral regions. The light is focused by lens 2 and directed through gas vessel 3 through which also the gas to be measured is being conducted. A concave mirror provided at the other side of radiation source 1 may be substituted for lens 2. Behind gas vessel 3 the light beam falls on detecting device 4 wherefrom electrical signals are transmitted to be processed in an electronic unit 5 for indication by an indicator 6 and/or for printing.

The detecting device 4 is designed as a constructional unit of uniform size for the entire measuring range to be covered, and the varying number of gases to be measured simultaneously. Due to this design, the gas measuring apparatus can be adapted to a specific measuring problem by exchanging the detecting unit.

Detecting unit 4 comprises prism 7 with at least two light-exit or incidence faces 8, 9 forming an angle with each other, at least one collective lens 10, two optical filters 11, and detectors 12. The prism 7 is symmetrical about a plane which extends parallel to the radiation path from source 1 and is made in one piece.

Figure 2:
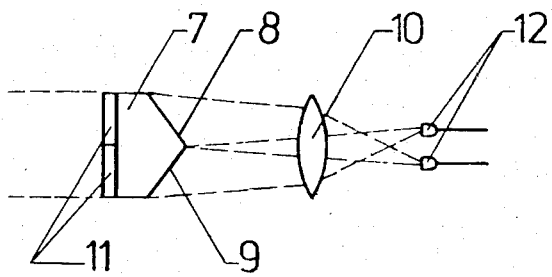
FIG. 2 is a schematic representation of another embodiment of the detecting device used in the device shown in FIG. 1.
Figure 3:
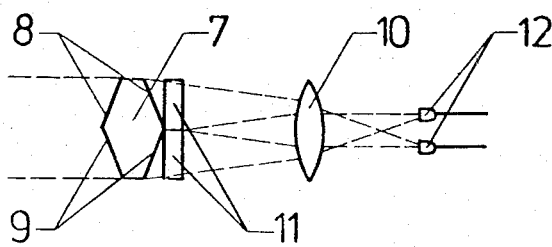
FIGS. 3, 4 and 5 are views similar to FIG. 2 of further embodiments of the detecting device.
Figure 4:
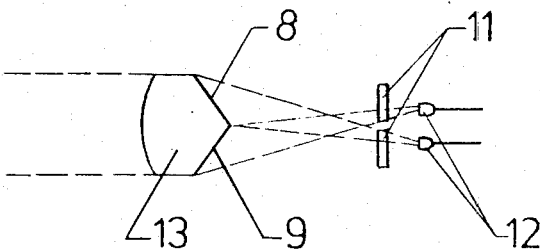
Figure 5:
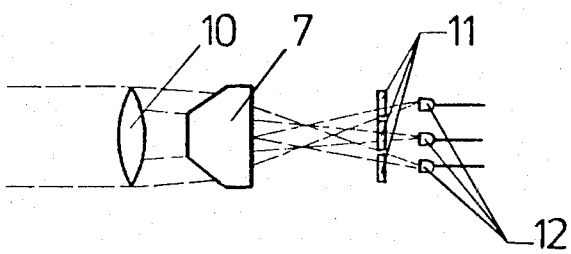

FIGS. 2 to 5 show examples of alternatives in the arrangement of elements of detecting unit 4, with FIGS. 2, 3, 4 being applicable to 2-beam devices, and FIG. 5 to a three-beam device. According to FIG. 2, the optical filters 11, 11 are provided ahead of prism 7 and form therewith a compound element. They may be provided after prism 7, as shown in 3, or close ahead of detectors 12, according to FIGS. 4 and 5. Collective lens 10 may be positioned ahead of prism 7 as in FIG. 5, or after prism 7 as in FIGS. 2 and 3, or combined with the prism to a single element 13 according to FIG. 4.

Prism 7 may be designed with its angular faces 8 and 9 at the exit side, according to FIGS. 2 and 4, or at the side of incidence, according to FIG. 5, or at both sides as according to FIG. 3.

While specific embodiments of the invention have been shown and described in detail to illustrate the application of the principles of the invention, it will be understood that the invention may be embodied otherwise without departing from such principles.

What is claimed is:

1. An optical multi-beam gas measuring apparatus for measuring proportions of a gas mixture, comprising: a gas vessel through which a gas mixture to be measured is directed; means for directing a radiation through said gas vessel; a detecting device in the path of said radiation following the gas vessel, said detecting device including a one piece prism for splitting said radiation into a plurality of beam paths, said prism being symmetrical about a plane which is parallel to the path of said radiation, a collective lens for focusing radiation of said beam paths, an optical filter in each beam path and detection means associated with each of said beam paths for detecting radiation of said beam paths, said detecting device being changeable as a unit; an electronic unit connected to said detection means for generating signals; and an indicating unit connected to said electronic unit for indicating specific gases.

2. An optical measuring apparatus according to claim 1, wherein said optical filters and said prism form a compound element.

3. An optical measuring apparatus according to claim 1, wherein said optical filters are located directly behind said prism.

4. An optical measuring apparatus according to claim 1, wherein said prism and said collective lens form a single element.

5. An optical measuring apparatus according to claim 1, wherein said collective lens is arranged ahead of said prism.

6. A method of measuring a gas mixture, comprising directing a radiation through the gas mixture and passing the radiation after it passes through the gas mixture through a one piece prism which is symmetrical about a plane which is parallel to the radiation to split it into a plurality of discrete radiation beams, using a collective lens to focus the beams, passing each beam through an optical filter and arranging an electrical detector in each of the beams passing through the optical filter to detect the characteristic of the gas mixture.

* * * * *